US00PP26990P3

(12) United States Plant Patent
Clark

(10) Patent No.: US PP26,990 P3
(45) Date of Patent: Aug. 2, 2016

(54) BLACKBERRY PLANT NAMED 'APF-153T'

(50) Latin Name: ***Rubus* subgenus *Rubus* Watson**
Varietal Denomination: APF-153T

(71) Applicant: THE BOARD OF TRUSTEES OF THE UNIVERSITY OF ARKANSAS, Little Rock, AR (US)

(72) Inventor: John Reuben Clark, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 275 days.

(21) Appl. No.: 14/120,553

(22) Filed: Jun. 3, 2014

(65) Prior Publication Data

US 2015/0351297 P1 Dec. 3, 2015

(51) Int. Cl.
*A01H 5/08* (2006.01)

(52) U.S. Cl.
USPC ..... Plt./203

(58) Field of Classification Search
USPC ..... Plt./203
CPC ..... A01H 5/0887
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark et al. |
| PP11,885 | P2 | 5/2001 | Clark et al. |
| PP14,935 | P2 | 6/2004 | Clark |
| PP15,788 | P2 | 6/2005 | Clark |
| PP16,989 | P3 | 8/2006 | Clark et al. |
| PP17,162 | P3 | 10/2006 | Clark et al. |
| PP17,983 | P2 | 9/2007 | Cabrera Avalos |
| PP20,891 | P3 | 3/2010 | Clark |
| PP22,449 | P3 | 1/2012 | Clark |
| PP24,249 | P3 | 2/2014 | Clark |
| 2014/0090122 | P1 | 3/2014 | Clark |
| 2015/0020246 | P1 | 1/2015 | Clark |

OTHER PUBLICATIONS

Clark, J.R., "Division develops first thornless priniocane blackberry," University of Arkansas System Division of Agriculture—Research and Extension website, Jul. 1, 2013, http://arkansasagnews.uark.edu/7751.htm.
Clark, J.R. et al., "'APF-45' Primocane-fruiting blackberry," (2011) Hort. Science 46(4):670-673.
Ruple, A. et al., "An evaluation of fertility in Arkansas prirnocane-fruiting blackberries," (2010) Hort. Science 45:1-6.
U.S. Appl. No. 13/998,724, filed Nov. 27, 2013.
Website for Heaven Can Wait Blackberry, http://www.gurneys.com/product/heaven_can_wait_blackberry, downloaded Oct. 15, 2014.
Office Acton dated Oct. 23, 2014 for U.S. Appl. No. 13/573,628 (13 pages).
Office Acton dated Dec. 17, 2014 for U.S. Appl. No. 13/987,214 (18 pages).

*Primary Examiner* — Kent L Bell
(74) *Attorney, Agent, or Firm* — Andrus Intellectual Property Law, LLP

(57) ABSTRACT

Description and specifications of a new and distinct blackberry cultivar named 'APF-153T' which originated from seed produced by a hand-pollinated cross of Ark. Selection A-2301T (non-patented, unreleased genotype)×APF-49T (non-patented, unreleased genotype) is provided. This new blackberry cultivar can be distinguished by its very large attractive fruit, very good flavor, excellent plant health, very early ripening, thornless, erect canes and primocane fruiting habit.

5 Drawing Sheets

Latin name: *Rubus* subgenus *Rubus* Watson.

BACKGROUND

The new primocane-fruiting cultivar of blackberry called 'APF-153T' is described herein. The new cultivar originated from a hand-pollinated cross of Ark. Selection A-2301T (unpatented selection)×APF-49T (unpatented selection) made in 2004. The seeds resulting from this controlled hybridization were germinated in a greenhouse in the spring of 2005 and planted in a field near Clarksville, Ark. (West-Central Arkansas). The seedlings fruited in the summer of 2007 and one seedling, designated APF-153T, was selected for its very large attractive fruit, very good flavor, excellent plant health, very early ripening, thornlessness, erect canes and primocane fruiting habit in 2007.

SUMMARY OF THE INVENTION

The new and distinct cultivar of blackberry originated from a hand-pollinated cross of Ark. Selection A-2301T (non-patented, unreleased genotype; female)×APF-49T (non-patented, unreleased genotype; male) made in 2004 and located near Clarksville, Ark. (West-Central Arkansas). The botanical designation of the new cultivar of blackberry is *Rubus* subgenus *Rubus* Watson. The seeds resulting from this controlled hybridization were germinated in a greenhouse in the winter to early spring of 2005 and planted in a field near Clarksville, Ark. The seedlings fruited in the summer of 2007 on floricanes and one seedling, designated APF-153T, was selected for its very large fruit with, attractive fruit appearance, very good flavor, excellent plant health, very early ripening, thornless canes, and cane erectness. Its primocane-fruiting habit was confirmed later that summer by observing primocane flowers.

During 2007, the original plant selection was propagated asexually from root cuttings at the above-noted location, and a test row of 30 plants was established. Subsequently, a larger test planting has been established with asexually multiplied plants at the same location in Arkansas. Additionally, the cultivar has been tested at test plots in Watsonville, Calif., and at this location propagation was from root cuttings from the Clarksville, Ark. test plot plants.

The new cultivar has been asexually multiplied annually since 2005 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

Its primocane fruiting performance is substantially better in more moderate summer climates such as Watsonville, Calif., as evidenced by larger fruit weight and higher yields compared to Clarksville, Ark. The cultivar differs from most blackberry cultivars which are floricane fruiting.

BRIEF DESCRIPTION OF THE PHOTOGRAPHS

The accompanying photographs show typical specimens of the new variety in color as nearly true as it is reasonably possible to make in a color illustration of this character.

DETAILED DESCRIPTION OF THE NEW CULTIVAR 'APF-153T'

Figure 1:
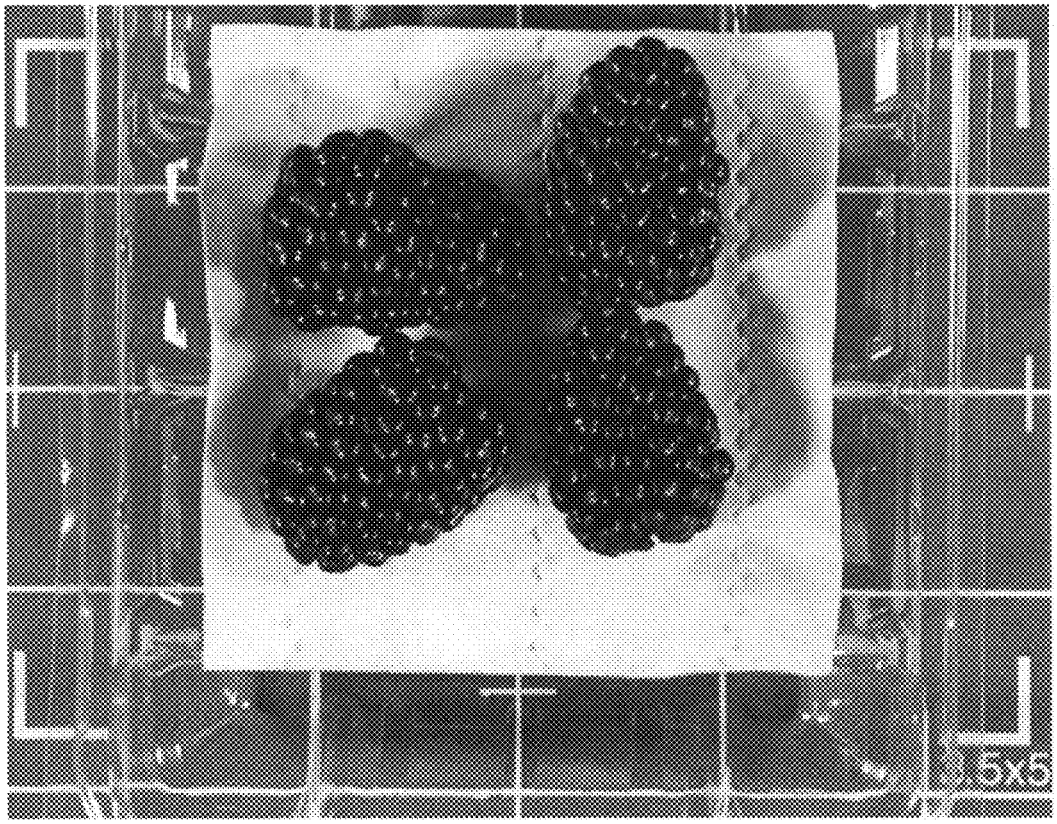
FIG. 1 is a photograph of three individual floricane fruit taken in late May, near Clarksville, Ark. of 'APF-153T'.
Figure 2:
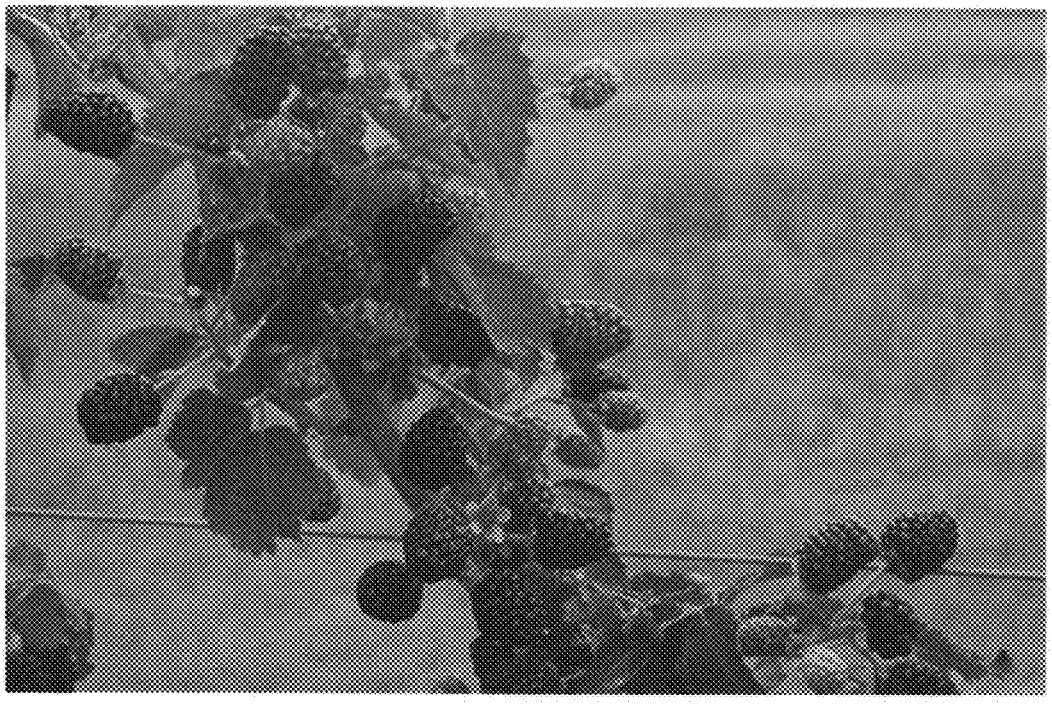
FIG. 2 is a photograph of fruits borne on a floricane taken in late May near Clarksville, Ark. of 'APF-153T'.
Figure 3:
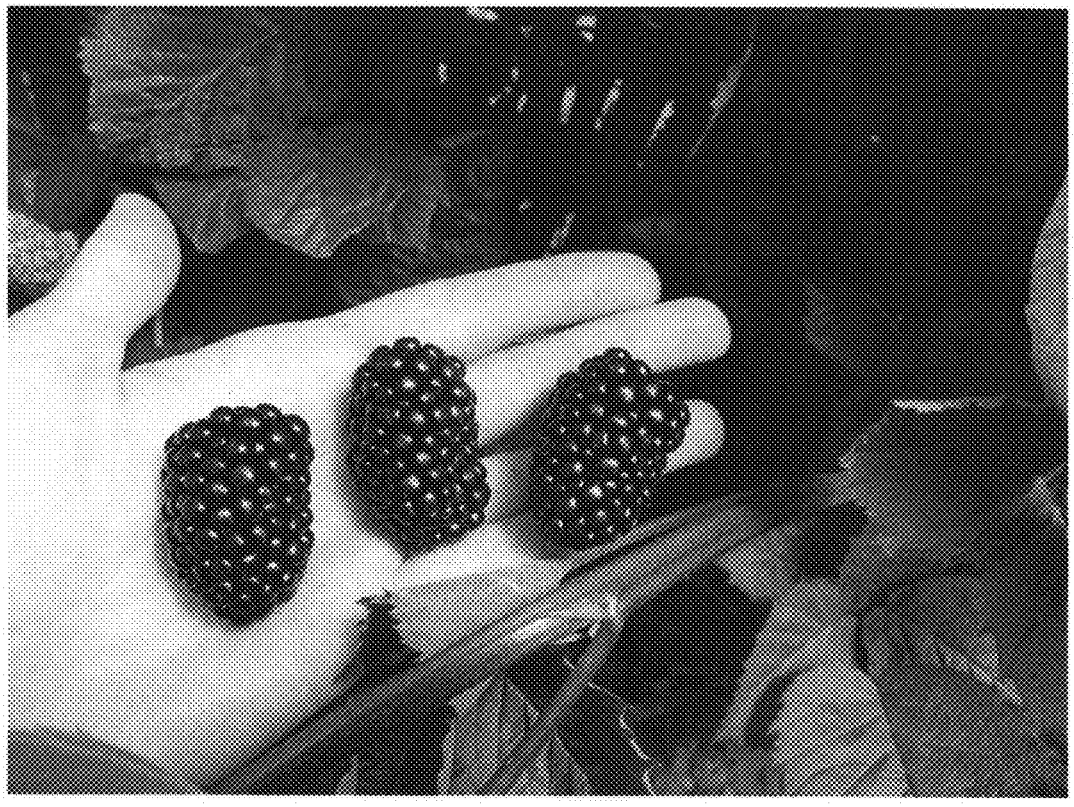
FIG. 3 is a photograph of primocane fruit being held near a thornless primocane taken in August in Watsonville, Calif. of 'APF-153T'.
Figure 4:
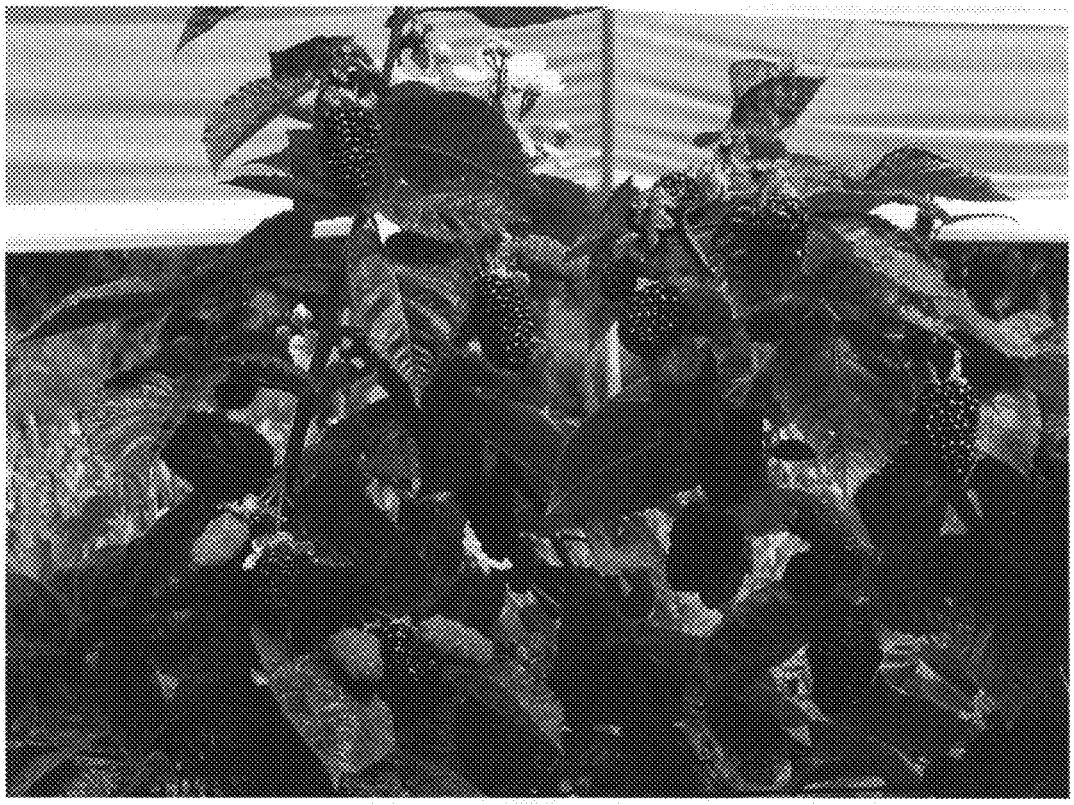
FIG. 4 is a photograph of fruit produced on a primocane taken in August in Watsonville, Calif. of 'APF-153T'.
Figure 5:
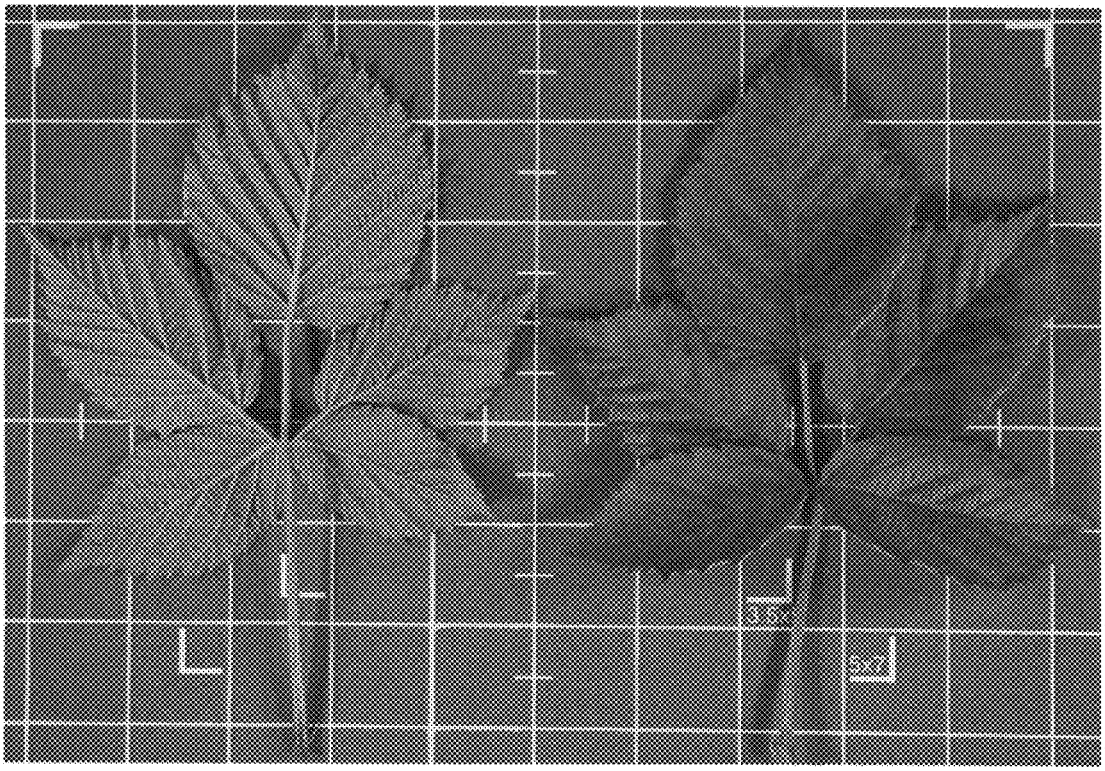
FIG. 5 is a photograph showing the abaxial (lower) and adaxial (upper) sides of primocane leaves of 'APF-153T'.

Plants and fruit of this new cultivar differ phenotypically from its parents. The new cultivar fruits on primocanes, has larger fruit, and ripens earlier than parent A-2301T, and fruit is larger and has increased levels of primocane fruiting than parent APF-49T. Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes can be trained to a self-supporting hedgerow although it is beneficial to use a trellis with supporting wires to prevent canes from falling over due to wind or heavy fruit loads. The plants are thornless. Plants and fruit are moderately resistant to anthracnose [*Elsinoe veneta* (Burkh.) Jenkins], and plants appear immune to orange rust [*Gymnoconia nitens* (Schwein.) F. Kern and H. W. Thurston.]. No screening has been done for resistance to double blossom/rosette [*Cercosporella rubi* (Wint.) Plakidas]

The floricane bloom period of the new cultivar begins on 10 April, compared to 17 April for 'APF-45' (U.S. Plant Pat. No. 22,449) and is shorter in length compared to 'APF-45'. Primocane bloom period begins 15 June compared to 30 June for 'APF-45'.

Floricane fruit of the new cultivar begins ripening 28 May, 9 days earlier than 'APF-45', but has a shorter fruiting period of about 25-30 days compared to 'APF 45' of 40 days. Primocane first ripe fruit date was 18-20 of July on tipped primocanes and ripened earlier than 'APF-45' of 8 August. At Watsonville, Calif. first ripe was 10-15 August with harvest extending into early October, compared to 'APF-45' which had first ripe date of 20 August.

Fruit yields of the new cultivar on floricanes are usually 1.4 kg/plant (3.1 lb) if the floricanes are retained for fruiting, compared to 1.8 kg/plant (4.0 lb) for 'APF-45' in West-Central Arkansas. Fruit yields of the cultivar on primocanes in West-Central Arkansas average 0.6 kg (1.5 lb/plant) compared to 0.8 kg (1.8 lb/plant) for 'APF-45' but in Watsonville, Calif. achieves 4-5.5 kg/plant (8.8 to 12.1 lb).

The fruit is elongated to blocky in shape, bright glossy black in color, and very attractive. The floricane fruit is large (9-13 g). Primocane fruit in West-Central Arkansas of the new cultivar averaged 8.8 g/berry while 'APF-45' averaged 5.8 g/berry but in Watsonville, Calif. ranged from 13-16 g/berry. Storage (shipping) potential of fresh fruit of the new cultivar is not as good compared to that of 'APF-45'.

The fresh fruit rates very good in flavor, comparable to 'APF-45' and 'Natchez' (U.S. Plant Pat. No. 20,891), but not as high as for 'Ouachita' (U.S. Plant Pat. No. 17,162) and higher than 'APF-12' (U.S. Plant Pat. No. 16,989). The flavor is sweet and mildly acidic, with a distinct blackberry aroma. The soluble solids concentration averages 9.7 to 10.5% on shiny black fruit harvested from floricanes but can extend to 13.2% for primocane fruit. Floricane fruit and flower clusters are medium-large, cymose, and are mostly borne on the periphery of the plant canopy, providing easy access to harvest. Flower fertility is high and clusters are well filled.

Primocane fruit and flowers are borne on the cane terminus or on lateral branches if primocanes are tipped, and fruiting continues down the primocane during the season. Canes usually attain a length of 4.5 to 5.0 ft prior to the appearance of flower buds. The number of nodes down the cane that develop flowers is largely dependent on the length and conditions of the late summer to fall growing period.

The following is a detailed description of the botanical and pomological characteristics of the subject blackberry. Color data are presented in Royal Horticultural Society Colour Chart designations (1986 2nd edition). Where dimensions, sizes, colors, and other characteristics are given, it is to be understood that such characteristics are approximations of averages set forth as accurately as practicable.

Plants used for botanical data were three years old and grown on a fine sandy loam soil with trickle irrigation near Clarksville, Ark. The plants were fertilized near budbreak (late March on average) with complete or nitrogen fertilizer, and had an additional nitrogen fertilizer application in early July. Primocanes were tipped at approximately 45 inches, and grown in a hedgerow training system. Weeds were controlled with pre- and post-emergence herbicides supplemented with mechanical weed control activities. A single application of liquid lime sulfur was applied to the plants at budbreak, but no other fungicides were used. The descriptions reported herein are from specimens grown near Clarksville, Ark. unless otherwise noted.

Plant:

*Size.*—Medium. Plants are grown in a hedgerow and primocanes tipped at approx., 107 cm; plants in this system range in size from approx. 107-140 cm tall and 91-102 cm wide.

*Growth habit.*—Moderate vigor, canes erect; suckers from crown and roots.

*Growth rate.*—First emergence of primocanes is 20 March and primocanes reach tipping height (107 cm) on 31 May.

*Productivity.*—Floricane — 1.4 kg/plant (3.1 lb) compared to 1.8 kg/plant (4.0 lb) for 'APF-45'. Primocane — 0.6 kg/plant (1.4 lb), compared to 0.8 kg/plant (1.8 lb) for 'APF-45' but in Watsonville, Calif. achieves 4-5.5 kg/plant (8.8 to 12.1 lb).

*Cold hardiness.*—Hardy to 8° (−13° C.) or lower, comparable to 'APF-45'. The low temperature of 8° F. was the lowest the cultivar has been exposed to and fruited successfully after this exposure.

*Canes.*—Thornless, erect. Floricane (dormant or winter cane): Cane diameter: base 2.02 cm; midpoint 1.69 cm; terminal 1.30 cm. Internode length: base 14.52 cm; midpoint 5.50 cm; terminal 4.84 cm. Floricane color: base Red-Purple Group (59A) over Yellow Green Group (146A); midpoint Red Purple Group (59A) over Green Group (139B); terminus Green Group (139C). Primocane (current-season cane): Cane diameter: base 1.90 cm; midpoint 1.74 cm; terminal 1.37 cm. Internode length: base 8.23 cm; midpoint 4.14 cm; terminal 4.28 cm. Primocane color: base Red Purple Group (61A) over Green Group (143B); midpoint Red Purple Group (58A) over Yellow Green Group (146C); terminus Red Purple Group (66C) over Green Group (141C). Date of primocane emergence: 20 March.

*Disease resistance.*—Moderate resistance to anthracnose, and plants appear immune to orange rust. No screening has been done for resistance to double blossom/rosette.

Foliage:

*Primocane.*—Leaves: large; mature compound leaf width 27.36 cm; length 16.90 cm. Leaflet: Width 11.51 cm; length 13.34 cm; shape ovate with acuminate apex and round base; margin doubly serrated, serration teeth length 0.28 cm and width 0.32 cm; pubescence is very light on abaxial surface and none on the adaxial surface; number of leaflets per compound leaf 5. Color: Base abaxial Green Group (137C); adaxial Green Group (137A); midpoint abaxial Green Group (138A); adaxial Green Group (139A); terminal abaxial Green Group (137A); adaxial Green Group (137D). Petioles: Length: 6.03 cm; color: Yellow-Green Group (144C); texture is very light to no pubescence. Petiolules: Length: 2.67 cm; color: Red Purple Group (59B) over Yellow Green Group (144C); texture is very light to no pubescence. Stipules: Length: 1.45 cm; width: 0.15 cm; texture is lightly pubescent.

*Floricane.*—Leaves: Medium; mature compound leaf width 21.09 cm; length 13.36 cm. Leaflet: Width 9.69 cm; length 10.12 cm; shape elongated ovate with acuminate apex and rounded to flat base; margin doubly serrated, with serration teeth length 0.42 cm and width at base 0.63 cm; pubescence is lightly present on abaxial side only. Number of leaflets per compound leaf is usually 3. Color: base abaxial Green Group (137C); adaxial Green Group (137A); midpoint abaxial Green Group (132B); adaxial Green Group (136B); terminal abaxial Green Group (138A); adaxial Green Group (139A). Petioles: Length 7.12 cm; color: Green Group (134A); texture has no pubescence. Petiolules: Length 1.63 cm; color: Green Group (146B); texture is very light to no pubescence. Stipules: Length 1.16 cm; width: 0.30 cm; texture is very pubescent.

Flowers:

*Floricane.*—Date of bloom: 10% bloom 10 April, compared to 17 April for 'APF-45'; 50% bloom 16 April compared to 'APF-45' on 26 April. Petal color: Red Purple Group (69B) over White Group (155D). Reproductive organs: Stamens — erect, numerous. Pistils — numerous. Pollen — normal, fertile, and abundant. Flower diameter: 3.02 cm. Petal size: Length 1.78 cm; width 1.35 cm. Average number flowers per cluster: 6. Average number of petals per flower: 5 to 6. Number of sepals per flower: 5. Peduncle length: 1.15 cm. Peduncle color: Yellow-Green Group (146D). Cyme type: Elongate simple dichasium cyme.

*Primocanes.*—Date of bloom: First bloom 15 June compared to 30 of June for 'APF-45', and can extend until frost depending on environment and cultural management. Petal color: White Group (155D). Reproductive organs — Stamens — numerous. Pistils — numerous. Pollen — fertile and abundant unless temperatures exceed 85 to 90° F. where pollen production can be reduced. Flower diameter: 3.02 cm. Petal size: Length: 1.78 cm; width: 1.35 cm. Average number flowers per cluster: 6, with a range of 5 to 10. Average number of petals per flower: 5 to 6. Number of sepals per flower: 5. Peduncle length: 1.15 cm. Peduncle color: Yellow-Green Group (146D). Cyme type: Elongate simple dichasium cyme.

Fruit:

*Floricane.*—Maturity — Average first ripe date 28 May, 9 days earlier than 'APF-45', but has a shorter fruiting period of about 25-30 days compared to 'APF 45' of 40 days. Size: Large, average 7-11 g. Diameter of fruit at primary position on inflorescence: equator 2.00 cm; base pole 1.60 cm; terminal pole 0.94 cm. Diameter of fruit at secondary positions on inflorescence: equator 2.34 cm; base pole 1.92 cm; terminal pole 1.38 cm. Length (primary fruit): 3.21 cm. Shape: elongated to blocky. Color: Black Group (202A). Drupelet size: 0.49 cm. Seed (drupe): average length; width; dry weight (50 seed weight); dry color; not yet available. Soluble solids: 9.7 to 10.5% on shiny black fruit. pH: 3.45. Acidity: 0.74% citric acid. Processed quality: Not evaluated for processing. Uses: Fresh market use for home gardens and local markets is the primary market due to poor postharvest performance for shipping.

*Primocane.*—Maturity — First ripe fruit date 18-20 of July on tipped primocanes and ripens earlier than 'APF-45' of 8 August and can fruit until frost depending on environment and cultural management; at Watsonville, Calif. first ripe was 10-15 August. Size: Large, 8.8 g/berry; in Watsonville, Calif. ranges from 13-16 g/berry. Diameter of fruit at primary position on inflorescence: equator (data not yet available) cm;

base pole (data not yet available) cm; terminal pole (data not yet available) cm. Diameter of fruit at secondary positions on inflorescence: equator (data not yet available) cm; base pole (data not yet available) cm; terminal pole (data not yet available) cm. Length (primary fruit): (data not yet available) cm. Shape: elongated to blocky. Color: Black Group (202A). Drupelet size: (data not yet available) cm. Seed (drupe): average length; width; dry weight (50 seed weight); dry color; not yet available. Soluble solids: up to 13.2%. pH: 3.47. Acidity: 0.63% citric acid. Processed quality: Not evaluated for processing.

Uses — Fresh market use for home gardens and local markets is the primary market due to poor postharvest performance for shipping.

The cultivar: The most distinctive features of the cultivar are very large attractive fruit, very good flavor, excellent plant health, very early ripening, thornless, erect canes and primocane fruiting habit.

I claim:

1. A new and distinct cultivar of blackberry plant named 'APF-153T', substantially as illustrated and described.

* * * * *